United States Patent

Wallroth et al.

[11] Patent Number: 6,095,137
[45] Date of Patent: Aug. 1, 2000

[54] ANESTHESIA RESPIRATOR

[75] Inventors: Carl F. Wallroth, Lübeck; Ernst Günter Scharmer, Krummesse, both of Germany; Jürgen Schröder, Doylestown, Pa.

[73] Assignee: Dräger Medizintechnik GmbH, Germany

[21] Appl. No.: 09/128,106

[22] Filed: Aug. 3, 1998

[30] Foreign Application Priority Data

Nov. 21, 1997 [DE] Germany .................. 197 51 597

[51] Int. Cl.⁷ .................................................. A61M 15/00
[52] U.S. Cl. ........................ 128/203.2; 128/205.28; 128/205.11
[58] Field of Search ................ 128/202.26, 203.13, 128/203.14, 203.25, 203.27, 205.11, 205.28, 910, 203.12

[56] References Cited

U.S. PATENT DOCUMENTS

| 3,868,225 | 2/1975 | Tidd ................................. 128/202.26 |
| 5,335,652 | 8/1994 | Falb et al. ......................... 128/203.14 |
| 5,806,513 | 9/1998 | Tham et al. ....................... 128/203.14 |

FOREIGN PATENT DOCUMENTS

94/08650   4/1994   WIPO ............................. 128/203.13

*Primary Examiner*—Glenn K. Dawson
*Attorney, Agent, or Firm*—McGlew & Tuttle, PC

[57] ABSTRACT

An anesthesia respirator for performing inhalation anesthesia is provided with a mobile, easy-to-refill oxygen source. To accomplish this object, an oxygen source is provided, which includes a plurality of chlorate candles (21, 22), which can be activated via respective igniters (23, 24).

6 Claims, 1 Drawing Sheet

ANESTHESIA RESPIRATOR

FIELD OF THE INVENTION

The present invention pertains to an anesthesia respirator as is used to carry out inhalation anesthesia.

BACKGROUND OF THE INVENTION

An anesthesia respirator with circulation of the breathing air and with control circuits for setting the anesthesia gas components to predetermined values has become known from DE 40 04 034 A1. The control circuits are designed essentially to maintain a quasi stationary operating state, i.e., the anesthetic gas components are maintained at previously set concentration values according to a control algorithm. To analyze the anesthesia components, an oxygen sensor, a carbon dioxide sensor, and an anesthetic sensor are arranged at different points of the breathing circuit. The anesthetic gas flows from a gas-metering unit for oxygen and laughing gas into the breathing circuit, wherein an inhalation anesthetic is also added to the breathing gas by means of an anesthetic-metering pump between the gas-metering unit and the breathing circuit. A control unit with integrated computing unit is the set point transducer for the gas-metering unit and the anesthetic-metering unit. The prior-art anesthesia respirator is supplied with gas from compressed gas cylinders or from a central gas supply system.

If the prior-art anesthesia respirator is operated from compressed gas cylinders, the duration of use in the case of mobile operation is limited by the capacity of the compressed gas cylinders carried with the anesthesia respirator. If is often difficult during mobile operation to refill a compressed gas cylinder on the site or to replace one with a full cylinder. This applies especially to the use of the apparatus under emergency conditions.

Chlorate candles, which burn off spontaneously after ignition and release oxygen due to the thermal decomposition of the chemical, have been known as oxygen sources. Such chlorate candles are used, e.g., to supply oxygen for passengers onboard airplanes. The passengers receive the oxygen via breathing masks, which are accommodated above the passenger seats in a container, which is automatically opened when the pressure drops in the passenger compartment. Such a device has been known from U.S. Pat. No. 3,981,300.

SUMMARY AND OBJECTS OF THE INVENTION

The primary object of the present invention is to provide an anesthesia respirator with a mobile oxygen source, which can be refilled in a simple manner.

According to the invention, an anesthesia respirator including a breathing gas line and an oxygen source comprising a plurality of chlorate candles with corresponding igniting means. A reservoir is provided taking up the oxygen generated by the chlorate candles. The reservoir is provided with a pressure-measuring means. A first control unit is provided which is connected to the pressure-measuring means and compares the measured pressure with a preset pressure value and sends a control signal, which activates the igniting means when the actual value is below the preset pressure value. A first metering valve is provided between the oxygen source and the breathing gas line. A second metering valve is provided between a gas supply line and the breathing gas line for metering ambient air. A measuring means is provided for determining at least the oxygen concentration in a section of the breathing gas line. A second control unit is connected to said measuring means and the metering valves. The second control unit actuates the metering valves corresponding to the measured oxygen concentration, such that a predetermined oxygen concentration becomes established at least in the section of the breathing gas line.

The advantage of the present invention is essentially that a predetermined oxygen concentration, which is suitable for performing inhalation anesthesia, can be set in the breathing gas line by using a plurality of chlorate candles, which are ignited as needed, by mixing the oxygen generated with ambient air, by monitoring the oxygen concentration in the breathing gas line, and by changing the mixing ratio of ambient air to the oxygen generated. The breathing gas line is defined as the connection line between a breathing gas source, e.g., the oxygen source, and the connection at the patient. It is especially advantageous in the respirator proposed according to the present invention that spent chlorate candles can be replaced in a simple manner, so that the replacement may also be performed during the operation, without such a replacement leading to an interruption in oxygen supply. Moreover, chlorate candles store well if they are sealed in a water-repellent protective layer and are thus protected from moisture.

A xenon gas source is advantageously connected to the gas supply line. Anesthesia with the gases xenon and oxygen is possible in this configuration of the anesthesia respirator.

The anesthesia respirator according to the present invention is suitable for performing inhalation anesthesia in the so-called half-open or half-closed breathing system. While the respiration of the patient is performed without rebreathing in the half-open breathing system, rebreathing is performed in a breathing circuit in the half-closed system. In the case of respiration in the half-closed breathing system, it is advantageous to remove excess inhalation anesthetic by means of an activated carbon filter that can be inserted into the breathing circuit. The activated carbon filter can be used advantageously when, e.g., the concentration of the inhalation anesthetic within the breathing circuit must be greatly reduced within a short time, or it must also be removed completely during the phase of conclusion.

The breathing circuit preferably has a breathing gas line containing an anesthetic gas delivery means, an anesthetic-metering means and an anesthetic gas escape valve, which are connected to the second control unit, as well as a carbon dioxide absorber.

An activated carbon filter, a bypass valve and a bypass line bridging over the said activated carbon filter are preferably provided in the breathing circuit. The flow of breathing gas can be deflected from the bypass line into the activated gas filter by means of the bypass valve.

The anesthesia respirator preferably includes means for determining the anesthetic concentration, the carbon dioxide concentration, and the airway pressure. The concentration determining means is connected to the measuring means in one assembly unit.

It is especially advantageous to fill the chlorate candles with different amounts of chemical, so that the oxygen production can be adapted to the instantaneous oxygen demand.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
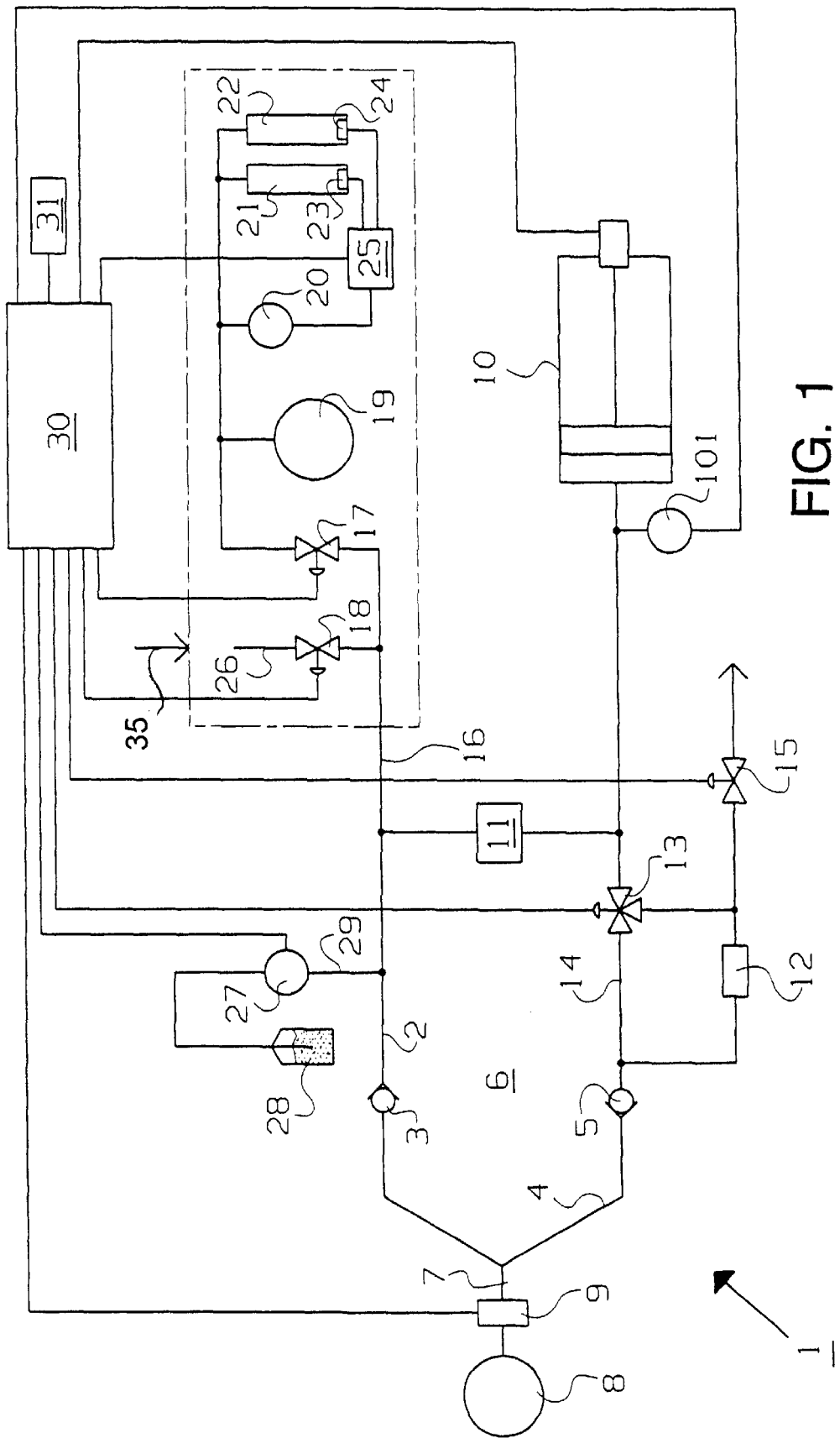
FIG. 1 is a system diagram of an anesthesia respirator according to the invention.

Referring to the FIG. 1 in particular, an anesthesia respirator 1 is shown with an inhalation line 2, an inhalation valve 3, an exhalation line 4 and an exhalation valve 5, which are assembled to form a breathing circuit 6. The inhalation line 2 and the exhalation line 4 are connected to a patient via a line 7. A measuring means 9 for determining the oxygen concentration, the anesthetic concentration, the airway pressure, and the carbon dioxide concentration in the breathing gas is arranged within the line 7.

A breathing gas delivery unit 10, which is connected to the breathing circuit and is provided with a pressure-monitoring means 101, ensures the delivery of the breathing gas through the inhalation line 2 to the patient 8. The breathing gas exhaled by the patient 8 returns via the exhalation line 4 into the breathing gas delivery unit 10 and again into the inhalation line 2 via a carbon dioxide absorber 11 located in the breathing circuit 6. An activated carbon filter 12, which can be switched into the flow path of the exhalation line 4 by means of a bypass valve 13 or can be bridged over by means of a bypass line 14, branches off from the exhalation line 4. Anesthetic is absorbed in the activated carbon filter 12. Excess breathing gas is released at the end of an exhalation stroke via the bypass valve 13 and an escape valve 15. The breathing gas that was used up during the breathing cycle or that escaped due to possible leakage can be replenished via a fresh gas line 16, which opens into the breathing circuit 6. To do so, a first metering valve 17 and a second metering valve 18 are provided in the fresh gas line 16. The first metering valve 17, which is used to meter oxygen, is connected to a reservoir 19, a pressure sensor designed as a level indicator 20 of the reservoir 19, as well as a first chlorate candle 21 and a second chlorate candle 22 acting as oxygen sources. The chlorate candles 21, 22 have igniters 23, 24, which can be actuated electrically and with which the thermal decomposition of the oxygen-generating chemical can be started. The igniters 23, 24 and the level indicator 20 are connected to a first control unit 25. After the igniter 23 of the first chlorate candle 21 has been activated by the first control unit 25, oxygen flows into the reservoir 19. The level indicator 20 records the pressure within the reservoir 19 and sends the measured pressure value to the first control unit 25. The measured pressure value is compared in the first control unit 25 with a preset value in order to start the second chlorate candle 22 by means of the igniter 24 when the measured value is below the preset value, if, e.g., oxygen has been metered into the breathing circuit 6 by means of the first metering valve 17 over a certain period of time. Only two chlorate candles 21, 22 are shown in the figure for greater clarity. It is especially advantageous to provide about four chlorate candles for generating oxygen, which are then activated one after the other.

Ambient air is metered into the breathing circuit 6 from a gas supply line 26 via the second metering valve 18 connected to the fresh gas line 16, and the oxygen concentration in the breathing gas present in the breathing circuit 6 can be influenced by changing the opening ratio of the metering valves 17, 18. The inhalation anesthetic needed to carry out inhalation anesthesia is drawn in from a storage tank 28 by means of a metering pump 27 and is fed into the breathing circuit 6 via an evaporating line 29. A xenon gas source 35 maybe connected to the gas supply line 26. The central control of the anesthesia respirator 1 is performed by means of a second control unit 30, to which the valves 13, 15, 17, 18, the measuring means 9, the breathing gas delivery unit 10, and the metering pump 27 are connected. Breathing parameters to be set, e.g., the respiration rate, the ratio of the inhalation time to the exhalation time, the breathing stroke volume, and the oxygen concentration, can be entered as set points in the second control unit 30 via a control panel 31.

The anesthesia respirator 1 according to the present invention operates as follows: Corresponding to the set points set on the control panel 31 for the respiration rate, the ratio of the inhalation time to the exhalation time, and the breathing stroke, the breathing gas delivery unit 10 performs individual breathing strokes. An oxygen-air breathing gas mixture enters the breathing circuit 6 via the fresh gas line 16, and an amount of inhalation anesthetic preset by the second control unit 30 is fed into the breathing circuit 6 by means of the metering pump 27. The breathing gas pressure, the oxygen concentration, the anesthetic concentration, and the carbon dioxide concentration are continuously measured in the line 7 leading to the patient 8 with the measuring means 9, and they are compared in the second control unit 30 with preset values, i.e., with an oxygen concentration set point, an anesthetic concentration set point, and a carbon dioxide concentration set point. If, e.g., the measured oxygen concentration is below the oxygen concentration set point, the first metering valve 17 is opened more widely, so that more oxygen will flow from the reservoir 19 into the fresh gas line 16 and the gas flow through the first metering valve 17 will be reduced. As an alternative, the second metering valve 26 can be opened more widely, without changing the position of the first metering valve 17, as a result of which more ambient air is mixed with the breathing gas.

If the measured anesthetic concentration deviates from the anesthetic concentration set point, the amount of anesthetic introduced by the metering pump 27 into the breathing circuit 6 is increased or decreased by the second control unit 30.

The carbon dioxide concentration determined by the measuring means 9 can be influenced essentially by the nature of the respiration, i.e., the respiration rate of the breathing gas delivery unit 10. The respiration rate is increased or decreased correspondingly if the measured carbon dioxide concentration deviates from the carbon dioxide concentration set point.

The pressure within the breathing gas delivery unit 10 is monitored by means of the pressure-monitoring means 101 connected to the second control unit 30 such that when the pressure drops below a preset value, e.g., as a consequence of deficiency of gas in the breathing circuit 6 at the end of the exhalation, the second metering valve 18 is kept open until the deficiency of gas is compensated.

The anesthetic concentration in the breathing circuit 6 shall be reduced as quickly as possible during the phase of conclusion of the anesthesia. To do so, the metering pump 27 is first switched off by the second control unit 30, and the bypass valve 13 is set such that the total gas flow of the exhalation line 4 is passed through the activated carbon filter 12. The inhalation anesthetic is adsorbed on the activated carbon in the activated carbon filter 12 in the known manner.

While a specific embodiment of the invention has been shown and described in detail to illustrate the application of the principles of the invention, it will be understood that the invention may be embodied otherwise without departing from such principles.

What is claimed is:

1. An anesthesia respirator, comprising:

a breathing gas line;

an oxygen source comprising a plurality of chlorate candles with corresponding igniting means;

a reservoir connected to said oxygen source for taking up the oxygen generated by said oxygen source;

a pressure-measuring means connected to said reservoir, providing a measured pressure value;

a first control unit connected to said pressure-measuring means, said first control unit comparing the measured pressure value with a preset pressure value and sending a control signal which activates said igniting means when the measured pressure value is below the preset pressure value;

an ambient air gas supply line;

a first metering valve between said oxygen source and said breathing gas line;

a second metering valve between said gas supply line and said breathing gas line for metering ambient air;

a measuring means for determining an oxygen concentration in a section of said breathing gas line; and a second control unit connected to said measuring means for determining an oxygen concentration and connected to said first metering valve and said second metering valve for actuating said first metering valve and said second metering valve corresponding to the measured oxygen concentration, such that a predetermined oxygen concentration becomes established at least in said section of said breathing gas line.

2. The anesthesia respirator in accordance with claim 1, wherein a xenon gas source is connected to said gas supply line.

3. The anesthesia respirator in accordance with claim 1, further comprising:

anesthetic gas delivery means;

anesthetic-metering means;

an anesthetic gas escape valve; and a carbon dioxide absorber, wherein said breathing gas line forms a part of a breathing circuit containing said anesthetic gas delivery means, said anesthetic-metering means, and said anesthetic gas escape valve, which are connected to said second control unit, as well as said carbon dioxide absorber.

4. The anesthesia respirator in accordance with claim 3, further comprising:

a bypass valve; and a bypass line, wherein said bypass valve and said bypass line bridge over an activated carbon filter in said breathing circuit, wherein the flow of breathing gas can be deflected from said bypass line into said activated carbon filter by means of said bypass valve.

5. The anesthesia respirator in accordance with claim 1, further comprising means for determining the anesthetic concentration, the carbon dioxide concentration, and the airway pressure connected to said measuring means for determining an oxygen concentration in one assembly unit.

6. The anesthesia respirator in accordance with claim 1, wherein said chlorate candles are each filled with different amounts of chemical.

* * * * *